(12) United States Patent
Chiu et al.

(10) Patent No.: US 7,994,449 B2
(45) Date of Patent: Aug. 9, 2011

(54) SQUARE-WAVE LASER BONDING

(75) Inventors: Jessica Chiu, Palo Alto, CA (US); Lara K. Suh, Redwood City, CA (US); Arthur Wen, Sunnyvale, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1544 days.

(21) Appl. No.: 11/137,869

(22) Filed: May 25, 2005

(65) Prior Publication Data

US 2005/0211679 A1    Sep. 29, 2005

Related U.S. Application Data (63) Continuation of application No. 10/328,794, filed on Dec. 23, 2002, now abandoned, which is a continuation of application No. 09/505,335, filed on Feb. 16, 2000, now abandoned.

(51) Int. Cl.
*B23K 26/00* (2006.01)
(52) U.S. Cl. .......... 219/121.64; 219/121.63; 219/121.79
(58) Field of Classification Search ............. 219/121.64, 219/121.63, 121.79, 121.78, 121.8, 121.81, 219/121.82
See application file for complete search history.

(56) References Cited

U.S. PATENT DOCUMENTS

| | | | |
|---|---|---|---|
| 547,732 A | 10/1895 | Marble | |
| 776,391 A | 11/1904 | Giese | |
| 1,260,690 A | 3/1918 | Liady | |
| 3,560,291 A | 2/1971 | Foglia et al. | |
| 3,769,117 A | 10/1973 | Bowen et al. | |
| 3,974,016 A | 8/1976 | Bondybey et al. | |
| 4,069,080 A | 1/1978 | Osborne | |
| 4,156,626 A | 5/1979 | Souder | |
| 4,195,637 A | 4/1980 | Grüntzig et al. | |
| 4,251,305 A | 2/1981 | Becker et al. | |
| 4,323,071 A | 4/1982 | Simpson et al. | |
| 4,515,651 A * | 5/1985 | MacLaughlin et al. | ....... 156/423 |
| 4,537,809 A | 8/1985 | Ang et al. | |
| 4,581,017 A | 4/1986 | Sahota | |

(Continued)

FOREIGN PATENT DOCUMENTS

DE    9102312    8/1992

(Continued)

OTHER PUBLICATIONS

PCT Search Report PCT/US 99/03327, mailed Jun. 18, 1999.

(Continued)

*Primary Examiner* — M. Alexandra Elve
(74) *Attorney, Agent, or Firm* — Blakely Sokoloff Taylor & Zafman LLP (57) ABSTRACT

The present invention provides a square-wave laser seal pattern made by first directing a laser beam onto an shaft while the shaft is moving in a horizontal direction relative to a laser device so as to create a horizontal laser seal bond segment. Next, with the shaft rotating about a shaft longitudinal axis, the laser beam is directed onto the shaft so as to create a vertical laser seal bond segment. By alternately creating and coupling together a plurality of horizontal and vertical laser seal bond segments, a square-wave laser seal is formed around a circumference of the shaft. The shaft's movement in a horizontal direction relative to a laser beam may be either at a constant speed or a variable speed so as to control the amount of laser energy heat impacting the shaft material.

22 Claims, 4 Drawing Sheets

U.S. PATENT DOCUMENTS

| | | | |
|---|---|---|---|
| 4,661,094 A | 4/1987 | Simpson | |
| 4,697,575 A | 10/1987 | Horowitz | |
| 4,706,652 A | 11/1987 | Horowitz | |
| 4,733,047 A * | 3/1988 | Cruickshank et al. | 219/121.63 |
| 4,744,366 A | 5/1988 | Jang | |
| 4,748,982 A | 6/1988 | Horzewski et al. | |
| 4,762,130 A | 8/1988 | Fogarty et al. | |
| 4,763,671 A | 8/1988 | Goffinet | |
| 4,771,777 A | 9/1988 | Horzewski et al. | |
| 4,771,778 A | 9/1988 | Mar | |
| 4,775,371 A | 10/1988 | Mueller, Jr. | |
| 4,790,315 A | 12/1988 | Mueller, Jr. et al. | |
| 4,793,351 A | 12/1988 | Landman et al. | |
| 4,815,449 A | 3/1989 | Horowitz | |
| 4,828,599 A * | 5/1989 | Sachs et al. | 65/109 |
| 4,861,520 A | 8/1989 | van't Hooft et al. | |
| 4,913,701 A * | 4/1990 | Tower | 604/103 |
| 4,936,823 A | 6/1990 | Colvin et al. | |
| 4,940,064 A | 7/1990 | Desai | |
| 4,969,863 A | 11/1990 | van't Hooft et al. | |
| 4,976,720 A | 12/1990 | Machold et al. | |
| 4,983,167 A | 1/1991 | Sahota | |
| 4,994,560 A | 2/1991 | Kruper, Jr. et al. | |
| 4,998,917 A | 3/1991 | Gaiser et al. | |
| 5,002,560 A | 3/1991 | Machold et al. | |
| 5,015,230 A | 5/1991 | Martin et al. | |
| 5,019,042 A | 5/1991 | Sahota | |
| 5,032,113 A | 7/1991 | Burns | |
| 5,034,001 A | 7/1991 | Garrison et al. | |
| 5,040,543 A | 8/1991 | Badera et al. | |
| 5,046,503 A | 9/1991 | Schneiderman | |
| 5,059,166 A | 10/1991 | Fischell et al. | |
| 5,061,273 A | 10/1991 | Yock | |
| 5,084,002 A | 1/1992 | Liprie | |
| 5,087,246 A | 2/1992 | Smith | |
| 5,100,429 A | 3/1992 | Sinofsky et al. | |
| 5,111,995 A * | 5/1992 | Dumitrascu et al. | 239/542 |
| 5,133,956 A | 7/1992 | Garlich et al. | |
| 5,137,513 A | 8/1992 | McInnes et al. | |
| 5,151,149 A | 9/1992 | Swartz | |
| 5,176,617 A | 1/1993 | Fischell et al. | |
| 5,176,661 A | 1/1993 | Evard et al. | |
| 5,180,368 A | 1/1993 | Garrison | |
| 5,195,971 A | 3/1993 | Sirhan | |
| 5,199,939 A | 4/1993 | Dake et al. | |
| 5,213,561 A | 5/1993 | Weinstein et al. | |
| 5,226,889 A | 7/1993 | Sheiban | |
| 5,242,396 A | 9/1993 | Evard | |
| 5,246,752 A * | 9/1993 | Raczkowski | 428/35.7 |
| 5,258,419 A | 11/1993 | Rolando et al. | |
| 5,263,963 A | 11/1993 | Garrison et al. | |
| 5,267,960 A | 12/1993 | Hayman et al. | |
| 5,273,738 A | 12/1993 | Matthews et al. | |
| 5,279,562 A | 1/1994 | Sirhan et al. | |
| 5,282,781 A | 2/1994 | Liprie | |
| 5,295,959 A | 3/1994 | Gurbel et al. | |
| 5,295,960 A | 3/1994 | Aliahmad et al. | |
| 5,295,995 A | 3/1994 | Kleiman | |
| 5,300,281 A | 4/1994 | McMillan et al. | |
| 5,302,168 A | 4/1994 | Hess | |
| 5,306,246 A | 4/1994 | Sahatjian et al. | |
| 5,308,356 A | 5/1994 | Blackshear, Jr. et al. | |
| 5,315,483 A | 5/1994 | Tracy | |
| 5,320,824 A | 6/1994 | Brodack et al. | |
| 5,334,154 A | 8/1994 | Samson et al. | |
| 5,336,518 A | 8/1994 | Narayanan et al. | |
| 5,350,361 A | 9/1994 | Tsukashima et al. | |
| 5,352,199 A | 10/1994 | Tower | |
| 5,354,257 A | 10/1994 | Roublin et al. | |
| 5,356,506 A | 10/1994 | McNeil et al. | |
| 5,380,747 A | 1/1995 | Medford et al. | |
| 5,395,333 A | 3/1995 | Brill | |
| 5,405,622 A | 4/1995 | Vernice et al. | |
| 5,409,495 A | 4/1995 | Osborn | |
| 5,411,466 A | 5/1995 | Hess | |
| 5,415,664 A | 5/1995 | Pinchuk | |
| 5,425,710 A | 6/1995 | Khair et al. | |
| 5,441,516 A | 8/1995 | Wang et al. | |
| 5,447,497 A | 9/1995 | Sogard et al. | |
| 5,456,667 A | 10/1995 | Ham et al. | |
| 5,458,572 A | 10/1995 | Campbell et al. | |
| 5,484,384 A | 1/1996 | Fearnot | |
| 5,498,227 A | 3/1996 | Mawad | |
| 5,501,667 A | 3/1996 | Verduin, Jr. | |
| 5,501,759 A * | 3/1996 | Forman | 156/272.8 |
| 5,503,613 A | 4/1996 | Weinberger | |
| 5,503,614 A | 4/1996 | Liprie | |
| 5,507,301 A | 4/1996 | Wasicek et al. | |
| 5,507,769 A | 4/1996 | Marin et al. | |
| 5,516,336 A | 5/1996 | McInnes et al. | |
| 5,540,659 A | 7/1996 | Teirstein | |
| 5,542,925 A | 8/1996 | Orth | |
| 5,549,552 A | 8/1996 | Peters et al. | |
| 5,573,508 A | 11/1996 | Thornton | |
| 5,573,509 A | 11/1996 | Thornton | |
| 5,599,306 A | 2/1997 | Klein et al. | |
| 5,601,736 A | 2/1997 | Saitho et al. | |
| 5,607,607 A * | 3/1997 | Naiman et al. | 219/121.68 |
| 5,616,114 A | 4/1997 | Thornton et al. | |
| 5,618,266 A | 4/1997 | Liprie | |
| 5,643,171 A | 7/1997 | Bradshaw et al. | |
| 5,645,740 A * | 7/1997 | Naiman et al. | 219/121.68 |
| 5,653,691 A | 8/1997 | Rupp et al. | |
| 5,658,311 A | 8/1997 | Baden | |
| 5,683,345 A | 11/1997 | Waksman et al. | |
| 5,688,486 A | 11/1997 | Watson et al. | |
| 5,707,332 A | 1/1998 | Weinberger | |
| 5,714,290 A * | 2/1998 | Yu et al. | 430/56 |
| 5,730,698 A | 3/1998 | Fischell et al. | |
| 5,738,901 A | 4/1998 | Wang et al. | |
| 5,762,906 A | 6/1998 | Creighton | |
| 5,766,192 A | 6/1998 | Zacca | |
| 5,782,740 A | 7/1998 | Schneiderman | |
| 5,782,742 A | 7/1998 | Crocker et al. | |
| 5,797,869 A | 8/1998 | Martin et al. | |
| 5,797,948 A | 8/1998 | Dunham | |
| 5,826,588 A * | 10/1998 | Forman | 128/898 |
| 5,836,965 A | 11/1998 | Jendersee et al. | |
| 5,840,064 A | 11/1998 | Liprie | |
| 5,840,067 A | 11/1998 | Berguer et al. | |
| 5,851,171 A | 12/1998 | Gasson | |
| 5,863,284 A | 1/1999 | Klein | |
| 5,871,436 A | 2/1999 | Eury | |
| 5,882,290 A | 3/1999 | Kume | |
| 5,882,291 A | 3/1999 | Bradshaw et al. | |
| 5,899,882 A | 5/1999 | Waksman et al. | |
| 5,910,101 A | 6/1999 | Andrews et al. | |
| 5,938,582 A | 8/1999 | Ciamacco, Jr. et al. | |
| 5,947,924 A | 9/1999 | Liprie | |
| 5,951,458 A | 9/1999 | Hastings et al. | |
| 5,954,741 A | 9/1999 | Fox | |
| 5,961,765 A | 10/1999 | Kastenhofer | |
| 5,964,730 A | 10/1999 | Williams et al. | |
| 5,976,106 A | 11/1999 | Verin et al. | |
| 5,984,963 A | 11/1999 | Ryan et al. | |
| 6,131,266 A * | 10/2000 | Saunders | 29/557 |
| 6,201,216 B1 | 3/2001 | Mumaw | |
| 6,579,626 B1 * | 6/2003 | Ottinger et al. | 428/626 |

FOREIGN PATENT DOCUMENTS

| | | |
|---|---|---|
| DE | 4315002 C1 | 5/1993 |
| EP | 0633041 A1 | 1/1995 |
| EP | 0688580 A1 | 12/1995 |
| EP | 0801961 A2 | 10/1997 |
| EP | 0829271 A2 | 3/1998 |
| EP | 0865803 A2 | 9/1998 |
| EP | 0879614 A1 | 11/1998 |
| WO | WO-9217236 | 10/1992 |
| WO | WO-9304735 | 3/1993 |
| WO | WO-9425106 | 11/1994 |
| WO | WO-9519807 | 7/1995 |
| WO | WO-9526681 | 10/1995 |
| WO | WO-9606654 | 3/1996 |
| WO | WO-9610436 | 4/1996 |
| WO | WO-9614898 | 5/1996 |
| WO | WO-9619255 | 6/1996 |
| WO | WO-9707740 | 3/1997 |

| WO | WO-9737715 | 10/1997 |
| WO | WO-9740889 | 11/1997 |
| WO | WO-9801182 | 1/1998 |
| WO | WO-9801183 | 1/1998 |
| WO | WO-9801184 | 1/1998 |
| WO | WO-9801185 | 1/1998 |
| WO | WO-9839052 | 9/1998 |

OTHER PUBLICATIONS

PCT Search Report PCT/US 99/03343, mailed Jun. 17, 1999.
PCT Search Report PCT/US 99/03328, mailed Jun. 18, 1999.
PCT Search Report PCT/US 99/03329, mailed Jun. 18, 1999.
PCT Search Report PCT/US 99/03360, mailed Jun. 17, 1999.
Byhardt, Roger W., et al., "The Heart and Blood Vessels", *Radiation Oncology Rationale, Technique Results*, Jan. 1996, pp. 277-284.
Calfee, Ph.D., Richard V., "High Dose Rate Afterloader System for Endovascular Use-Neocardia", *Discoveries in Radiation for Restenosis, Abstract 39*, Jan. 1996, p. 119.
Condado, Jose A., et al., "Late Follow-up After Percutaneous Transluminal Coronary Angioplasty (PTCA) and Intracoronary Radiation Therapy (ICRT)", *Discoveries in Radiation for Restenosis, Abstract 34*, Jan. 1996, p. 105.
Dawson, Jr., M.D., John T., "Theoretic Considerations Regarding Low-Dose Radiation Therapy", *Texas Heart Institute Journal*, vol. 18, No. 1, 1991, pp. 4-7.
Fischell, M.D., Tim A., et al., "A Beta-Particle Emitting Radioisotope Stent for the Prevention of Restenosis", *Discoveries in Radiation for Restenosis, Abstract 23*, Jan. 1996, p. 65.
Fischell, M.D., Tim A., et al., "Low-Dose B-Particle Emission from 'Stent' Wire Results in Complete, Localized Inhibition of Smooth Muscle Cell Proliferation", Circulation, vol. 90, No. 6, Dec. 1994, pp. 2956-2963.
Friedman, Meyer, et al., "Effect of Iridium 192 Radiation on Thromboatherosclerotic Plaque in the Rabbit Aorta", *Arch Path*, vol. 80, Sep.1965, pp. 285-290.
Friedman, Meyer, et al., "The Antiatherogenic Effect of Iridium 192 Upon the Cholesterol-Fed Rabbit", *Journal of Clinical Investigation*, vol. 43, No. 2, 1964, pp. 185-192.
Haude, M.D., Michael, et al., "Quantitative Analysis of Elastic Recoil after Balloon Angioplasty and After Intracoronary Implantation of Balloon-Expandable Palmaz-Schatz Stents", *JACC*, vol. 21, No. 1, Jan. 1993, pp. 26-34.
Hehrlein, C, et al., "Radioactive Stents", *Discoveries in Radiation for Restenosis, Abstract 22*, Jan. 1996, pp. 63-64.
Hehrlein, M.D., Chrisoph, et al., "Low-Dose Radioactive Endovascular Stents Prevent Smooth Muscle Cell Proliferation and Neointimal Hyperplasia in Rabbits", *Circulation*, vol. 92, No. 6, Sep. 15, 1995, pp. 1570-1575.
Hoopes, D.V.M., Ph.D., Paul J., et al., "Intraoperative Irradiation of the Canine Abdominal Aorta and Vena Cava", *Int. J. Radiation Oncology Biol. Phys.*, vol. 13, May 1987, pp. 715-722.
Hunink, M.D., Maria G., et al., "Risks and Benefits of Femoropopliteal Percutaneous Balloon Angiplasty", *Journal of Vascular Surgery*, vol. 17, No. 1, Jan. 1993, pp. 183-194.
Johnson, Lewis W., et al., "Review of Radiation Safety in the Cardiac Catheterization laboratory", *Catheterization and Cardiovascular Diagnosis*, vol. 25, 1992, pp. 186-194.
Kakuta, M.D., Tsunekazu, "Differences in Compensatory Vessel Enlargement, Not Intimal Formation, Account for Restenosis After Angioplasty in the Hypercholesterolemic Rabbit Model", *Circulation*, vol. 89, No. 6, Jun. 1994, pp. 2809-2815.
Katzen, M.D., Barry T., "Mechanical Approaches to Restenosis in the Peripheral Circulation", Jan. 1996.
King, III, M.D., Spencer B., "Clinical Restenosis Trials Using Beta Energy Radiation", *Discoveries in Radiation for Restenosis, Abstract 32*, Jan. 1996, pp. 101-102.
Kunts, M.D., Richard E., et al., "Generalized Model of Restenosis After Conventional Balloon Angioplasty, Stenting and Directional Atherectomy", *JACC*, vol. 21, No. 1, Jan. 1993, pp. 15-25.
Li, Alexander N., et al., "A Novel Brachyehtapy Source for Treatment of Coronary Artery Restenosis", *Discoveries in Radiation for Restenosis, Abstract 24*, Jan. 1996, pp. 67-72.
Liermann, Dieter, et al., "Prophylactic Endovascular Radiotherapy to Prevent Intimal Hyperplasia After Stent Implantation in Femoropoliteal Arteries", *Cardiovascular and Interventional Radiology*, vol. 17, 1994, pp. 12-16.
Lindsay, Stuart, et al., "Aortic Arteriosclerosis in the Dog After Localized Aortic X-Irradiation", *Circulation Research*, vol., X Jan. 1962, pp. 51-60.
Lumsden, M.D., Alan B., et al., "Restenosis in Peripheral Vascular Disease", *Discoveries in Radiation for Restenosis, Abstract 28*, Jan. 1996, pp. 83-88.
March, M.D., Keith L., et al., "8-Methoxypsoraien and Longwave Ultraviolet Irradiation Are a Novel Antiproliferative Combination for Vascular Smooth Muscle", *Circulation*, vol. 87, No. 1, Jan. 1993, pp. 184-191.
Martin, M.D., Louis G., "Radiation for Peripheral Applications: Technical Aspects", *Discoveries in Radiation for Restenosis, Abstract 27*, Jan. 1996, pp. 81-82.
Popowski, M.D., Youri, et al., "Radioactive Wire in a Self-Centering Catheter System", *Discoveries in Radiation for Restenosis, Abstract 38*, Jan. 1996, pp. 117-118.
Schopohl, B, et al., "Endovascular Irradiation for Avoidance or Recurrent Stenosis After Stent Implantation in Peripheral Arteries-5 years Follow-up", *Discoveries in Radiation for Restenosis, Abstract 29*, Jan. 1996, pp. 89-92.
Schwartz, Robert S., et al., "Differential Neointimal Response to Coronary Artery Injury in Pigs and Dogs", *Arteriosclerosis and Thrombosis*, vol. 14, No. 3, Mar. 1994, pp. 395-400.
Schwartz, M.D., Robert S., et al., "Effect of External Beam Irradiation on Neointimal Hyperplasia After Experimental Coronary Artery Injury", *JACC*, vol. 19, No. 5, Apr. 1992, pp. 1106-1113.
Smith, III, Dr. Edward F., "Issues on Handling Radioactive Devices to Prevent Restenosis", *Discoveries in Radiation for Restenosis, Abstract 40*, Jan. 1996, pp. 121-122.
Soares, C. G., et al., "Measurement of Radial Dose Distributions Around Small Beta Particle Emitters Using High Resolution Radiochromic Foil Dosimetry",*Nuclear Technnology Publishing*, vol. 4, No. 1, 1992, pp. 367-372.
Teirstein, Paul S., et al., "Catheter-Based Radiation Therapy to Inhibit Restenosis Following Coronary Stenting", *Discoveries in Radiation for Restenosis, Abstract 31*, Jan. 1996, p. 99.
Unterberg, M.D., Christina, "Reduced Acute Thrombus Formation Results in Decreased Neointimal Proliferation After Coronary Angioplasty", *JACC*, vol. 26, No. 7, Dec. 1995, pp. 1747-1754.
Urban, M.D., Philip, et al., "Endovascular Irradiation with 90Y Wire", *Discoveries in Radiation for Restenosis, Abstract 33*, Jan. 1996, pp. 103-104.
Van'T Hooft, Eric, et al., "HDR Afterloader for Vascular Use", *Discoveries for Restenosis, Abstract 36*, Jan. 1996, p. 113.
Verin, M.D., Vitali, et al., "Intra-Arterial Beta Irradiation Prevents Neointimal Hyperplasia in a Hypercholesterolemic Rabbit Restenosis Model", *Circulation*, vol. 92, No. 8, Oct. 15, 1995, pp. 2284-2290.
Wagner, Ph.D., Louis K., et al., "Potential Biological Effects Following High X-Ray Dose Intervational Procedures", *Journal of Vascular and Interventional Radiology*, Jan.-Feb. 1994, pp. 71-84.
Waksman, M.D., Ron, "Catheter-Based Radiation in Stented Arteries", *Discoveries in Radiation for Restenosis, Abstract 25*, Jan. 1996, pp. 73-74.
Waksman, M.D., Ron, et al., "Endovascular Low-Dose Irradiation Inhibits Neointima Formation After Coronary Artery Balloon Injury in Swine", *Circulation*, vol. 91, No. 5, Mar. 1, 1995, pp. 1533-1539.
Waksman, M.D., Ron, et al., "Intracoronary Low-Dose B-irradiation Inhibits Neointima Formation After Coronary Artery Balloon Injury in the Swine Restenosis Model", *Circulation*, vol. 92, No. 10, Nov. 15, 1995, pp. 3025-3031.
Waksman, M.D., Ron, et al., "Intracoronary Radiation Before Stent Implantation Inhibits Neointima Formation in Stented Porcine Coronary Arteries", *Circulation*, vol. 92, No. 6, Sep. 15 1995, pp. 1383-1386.
Waksman, M.D., Ron, "Radiation in the Peripheral System at Emory", *Discoveries in Radiation for Restenosis, Abstract 30*, Jan. 1996, pp. 93-94.

Weintraub, M.D., William S., et al., "Can Restenosis After Coronary Angioplasty be Predicted From Clinical Variables?", *JACC*, vol. 21, No. 1, Jan. 1993, pp. 6-14.

Weldon, Thomas D., "Catheter Based Beta Radiation System", *Discoveries in Radiation for Restenosis, Abstract 35*, Jan. 1996, p. 111.

Weshler, Z , et al., "Inhibition by Irradiation of Smooth Muscle Cell Proliferation in the De-Endothelialized Rat Aorta", *Frontiers in Radiation Biology*, Oct. 1988, pp. 133-138.

Wiedermann, M.D., Joseph G., et al., "Effects of High-Dose Intracoronary Irradiation on Vasomotor Function and Smooth Muscle Histopathology", *Intracoronary Irradiation and Vasomotion*, 1994, pp. H125-H132.

Wiedermann, M.D., Joseph G., et al., "Intracoronary Irradiation Markedly Reduces Neointimal Proliferation After Balloon Angioplasty in Swine: Persistent Benefit at 6-month Follow-up", *JACC*, vol. 25, No. 1, May 1995, pp. 1451-1456.

Wiedermann, M.D., Joseph G., et al., "Intracoronary Irradiation Markedly Reduces Restenosis After Balloon Angioplasty in a Porcine Model", *JACC*, vol. 23, No. 6, May 1994, pp. 1491-1498.

\* cited by examiner

SQUARE-WAVE LASER BONDING

This application is a continuation of application Ser. No. 10/328,794 filed Dec. 23, 2002 now abandoned which is a continuation of parent application Ser. No. 09/505,335 filed Feb. 16, 2000 now abandoned.

BACKGROUND OF THE INVENTION

1. Field of the Invention

The present invention relates to providing tight seals along shafts by means of laser energy and more particularly to laser bonding of medical device shaft geometries.

2. Description of Related Art

Balloon catheters are well known for their utility in treating certain types of obstructions in blood vessels. In a Percutaneous Transluminal Coronary Angioplasty (PTCA or balloon angioplasty) procedure, catheters are inserted into the cardiovascular system. A pre-shaped guiding catheter is positioned in the coronary artery and then a dilatation catheter having a distensible balloon portion is advanced through the branches of the coronary artery until the balloon portion traverses or crosses a stenotic lesion. The balloon portion is then inflated with a fluid to compress the atherosclerosis in a direction generally perpendicular to the wall of the artery, thus dilating the lumen of the artery.

In the manufacture of balloon catheters and stent delivery systems, it is essential that the bonds between the catheter shaft and the balloon material be fluid tight and of sufficient strength to withstand the inflation fluid pressure. Typically, the balloon is mounted along the distal end region of the catheter body. In a multi-lumen balloon having a plurality of outer lumens disposed around a central lumen, the balloon outer lumens have tapered distal and proximal seal ends forming a fluted shaped balloon configuration. The balloon's proximal and distal seal ends are bonded to the catheter shaft via a proximal seal arrangement and a distal seal arrangement.

In some applications, including medical-related applications, two or more irregular shaped lumens or shafts must be bonded together so as to form a multi-lumen or multi-shaft assembly. Other applications may require that a material be bonded to a lumen or shaft that has an irregular shaped geometry.

There are several ways to bond a balloon to a catheter shaft, bond two or more lumens or shafts together into a multi-lumen or multi-shaft sub-assembly, or bond a material to an irregular shaped geometry.

One method to bond two or more lumens together into a multi-lumen sub-assembly or bond a material to an irregular shaped geometry is by using resistance heating of copper jaws. While the resistance jaws press the respective multi-lumens in the sub-assembly against each other the resistance jaws are heated until the lumens fuse. This method is particularly useful when bonding together shafts or lumens constructed of similar materials or of materials having similar material characteristics. However, this method provides unacceptable seals for when bonding components having multiple lumens, multiple shafts, or irregular geometries, for example, the non-circular geometry of the proximal and distal balloon seals of a multi-lumen balloon radiation centering catheter.

Another approach to bonding is to use adhesives or chemicals (i.e., solvent bonding). This approach is useful for multiple-lumen sub-assemblies being constructed of dissimilar materials. However, the adhesive layers add to the thickness of the area being bonded and increase its rigidity at the region of the bonds.

Yet another method for bonding is using a laser beam to target and heat up the region of interest until a seal is achieved. The laser seal configuration currently being used in most medical device applications has a helical or "rings" laser seal pattern. A laser beam is used to trace out a conventional "rings" pattern around the circumference of an area to be bonded such as where a balloon is being bonded to a catheter shaft. The helical laser seal pattern is achieved by directing a laser beam onto the balloon and catheter shaft while balloon and catheter shaft are rotated together about their longitudinal axis.

Figure 1:
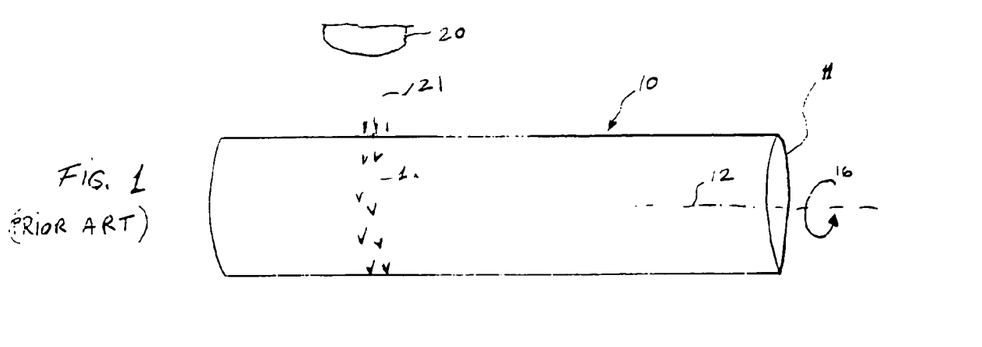
FIG. 1 illustrates a laser beam tracing out a conventional helical or rings-wave laser beam pattern (PRIOR ART).

FIG. 1 shows a prior art helical or "rings" laser seal pattern 1, where a laser beam 20 traces out the conventional "rings" pattern 1 around a circumference 11 of an irregular-shaped (e.g., a non-circular) geometrical component such as a multi-lumen shaft bundle 10. The prior art helical laser seal pattern 1 shown in FIG. 1 is achieved by directing a laser beam 21 onto the irregular shaped multi-lumen shaft bundle 10 while the shaft bundle 10 is rotated about its longitudinal axis 12.

This prior art helical laser seal pattern has a number of disadvantages. For example, when laser sealing an multi-lumen, multi-shaft, or irregular geometry, the helical laser sealing pattern is unable to fully achieve a fluid tight seal. In other words, where the configuration to be sealed is not circular, oval or has another simple geometry, the helical sealing pattern may not seal all the areas along such geometries properly. For example, a multi-lumen balloon has an irregular shape and has grooves (or flutes) between the lumens for providing perfusion when in use. The helical laser sealing pattern may not form a fluid tight seal within these grooves.

Thus, what is desired is a method and apparatus for forming a seal (or bond) in multiple lumen, multiple shaft, and/or irregular geometry configurations.

SUMMARY OF THE INVENTION

The present invention provides a square-wave laser seal pattern made by first directing a laser beam onto a shaft bundle while the shaft is moving in a horizontal direction relative to a laser device so as to create a horizontal laser seal bond segment. With the shaft rotating about a shaft longitudinal axis, the laser beam is directed onto the shaft so as to create a vertical laser seal bond segment. By alternately creating and coupling together a plurality of horizontal and vertical laser seal bond segments, a square-wave laser seal is formed around a circumference of the shaft.

BRIEF DESCRIPTION OF THE DRAWINGS

The present invention is illustrated by way of example and not limitation in the accompanying figures.

DETAILED DESCRIPTION OF THE INVENTION

A square-wave laser seal pattern and seal performed around the circumference of a shaft to bond materials and method for providing the same is described. The present invention improves the bonding and sealing of multiple lumen, multiple shaft, and irregular geometric components. For example, the present invention may be used to bond a material to a catheter shaft, where the conventional helical or rings laser seal pattern is unable to target and seal the material in the groove of a multiple lumen balloon.

The square-wave laser seal pattern of the present invention may be used in bonding components together, and is especially useful for bonding components of non-circular geometries such as multiple lumens and multiple shaft components as well as components with other irregular geometries. The square-wave laser seal pattern is also well suited to be used for performing the proximal and distal balloon seals for a single or multi-lumen balloon catheters, such as a multi-lumen balloon or radiation centering catheter. Furthermore, the square-wave laser seal pattern is well suited for use in other emerging products that have irregular shaft geometries that would make conventional laser sealing difficult.

In the following detailed description, numerous specific details are set forth in order to provide a more thorough understanding of the present invention. However, it will be apparent to those skilled in the art to which this invention pertains that the present invention may be practiced without these specific details. In other instances, well-known devices, methods, procedures, and individual components have not been described in detail so as not to unnecessarily obscure aspects of the present invention.

Figure 2:
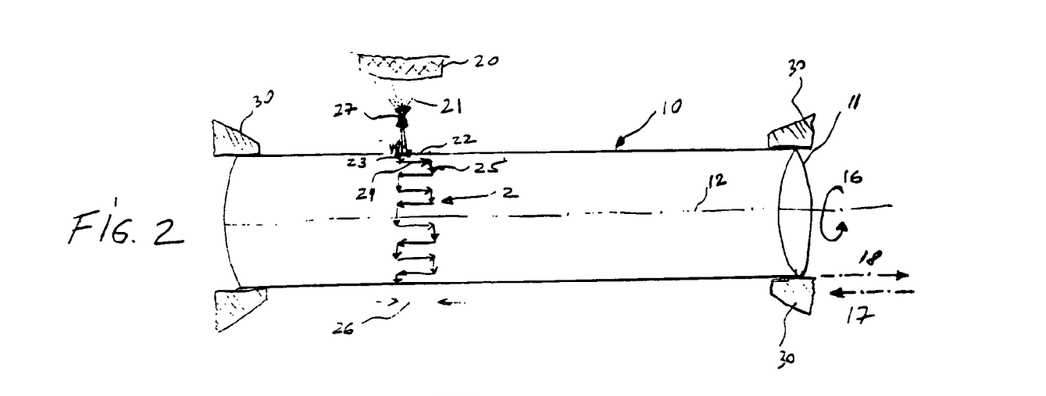
FIG. 2 illustrates the square-wave laser beam seal pattern of the present invention.

FIG. 2 shows the square-wave laser seal pattern 2 of the present invention. A laser beam 21 traces out a square-wave laser seal pattern 2 instead of the conventional helical or rings pattern 1 (of FIG. 1). The square-wave laser seal pattern 2, shown in FIG. 2, is achieved by directing a laser beam 21 onto a shaft 10, while the shaft 10 is alternately rotating about its longitudinal axis 12 and horizontally translating (i.e., horizontally moving) along its longitudinal axis 12. Alternating rotational movements and horizontal movements creates vertical laser seal bond segments and horizontal laser seal bond segments. The combination of vertical and horizontal laser seal bond segments creates an uninterrupted fluid tight seal around a circumference 11 of the shaft 10 (see FIG. 2).

Shaft 10 may be a conventional circular or oval shaft or may be a non-circular shaft such as a multi-lumen or multi-shaft bundle, or a shaft having other irregular geometries. For example, shaft 10 may be a catheter shaft having multiple lumens or a multiple lumen balloon that has an irregular geometry.

With reference to FIG. 2, in one embodiment, the square-wave laser seal pattern 2 is achieved by first directing a laser beam 21, emitted by laser device 20 (for example a $CO_2$ laser), onto a shaft 10. The shaft 10 is then moved at a constant speed in a first horizontal direction 17 relative to the laser device 20 so as to create a first horizontal laser seal bond segment 22. With the laser beam 21 still directed onto the shaft 10, the shaft 10 is then rotated in a circular direction 16 about its longitudinal axis 12 so as to create a first vertical laser seal bond segment 23. Next, with the laser beam 20 still directed onto the shaft 10, the shaft 10 is moved at a constant speed in a second horizontal direction 18 relative to the laser device 20 so as to create a second horizontal laser seal bond segment 24. In one embodiment of the presentation and for purpose of this example, the second horizontal direction 18 is opposite to the first horizontal direction 17. However, it should be noted that the direction of the horizontal movement may vary depending upon the geometry of the component being bonded. While still directing the laser beam 20 onto the shaft bundle 10, the shaft bundle is again rotated in the circular direction 16 about its longitudinal axis 12 so as to create a second vertical laser seal bond segment 25.

As shown on FIG. 2, to fully achieve the square-wave laser seal pattern 2 of this invention, the shaft 10 is alternately rotated about and horizontally translated (or moved) along the shaft 10 longitudinal axis 12 until the square-wave laser seal pattern 2 fully encircles the entire circumference 11 of the shaft 10. In this embodiment, the square-wave laser seal pattern essentially wraps around the circumference 11 of the shaft 10 (see FIG. 2). At least two horizontal laser seal bond segments (22, 24) and two vertical laser seal bond segments (23, 25) must be completed in order for the square-wave laser seal pattern 2 to fully encircle the entire circumference 11 of the shaft 10.

It should be noted that shaft 10, which is being held by a shaft holder fixture 30, is rotated along its longitudinal axis 12 in a circular direction 16 that may be in either a clockwise or counter-clockwise direction. Furthermore, to achieve the square-wave laser seal pattern 2 shown in FIG. 2, the seal pattern may either be started by initially creating a first horizontal laser seal bond segment 22 (as shown in FIG. 2) or by initially creating a first vertical laser seal bond segment 23. The direction of the initial laser seal bond segment, whether performed in a horizontal direction or a vertical direction, depends on the manufacturing preference and/or equipment specification.

It is also important to note that for the embodiment shown in FIG. 2, the laser device 20 emitting the laser beam 21 is held in a fixed position while a shaft holder fixture 30 holding the shaft 10 is in a movable configuration. Depending on the laser device configuration used and laser seal manufacturing preferences, in other embodiments the laser device 20 may be moved along and/or around the shaft 10 while the shaft 10 is kept either in a fixed or movable position by the shaft holder fixture 30.

In the example of a catheter shaft and a multi-lumen balloon, the lengths of the horizontal laser seal bond segments (22, 24) define a "width" 26 of the square-wave laser seal pattern shown in FIG. 2. The lengths of the horizontal laser seal bond segments (22, 24), and thus the square-wave laser seal "width" 26, are approximately 0.25 mm, with an upper range length limit of approximately 1.5 mm. These horizontal laser seal bond segment lengths are applicable to sealing irregular shaped shafts and balloons used in PTCA application, for example, a multi-lumen balloon radiation centering catheter. Larger horizontal laser seal bond segment lengths of between 0.5-5 mm may be used to seal irregular shaped shafts used in applications other than PTCA applications.

It should further be noted that shaft 10 being held by the shaft holder fixture 30, is generally incrementally rotated along its longitudinal axis 12 based on a preset degree of rotation 31 of the shaft holder fixture 30. Therefore, the lengths of the vertical laser seal bond segments (23, 25) are based on the preset degree of rotation 31 as well as the diameter of the shaft 10. The preset degree of rotation 31 represents the predetermined number of degrees of circular rotation for the shaft holder fixture 30 if these were measured around the circumference 11 of the shaft 10 (where one degree of circular rotation equals $1/360$ of the circumference 11 of the shaft 10). The larger the preset degree of rotation 31 is, the larger the lengths of the vertical laser seal bond segments (23, 25) will be. For the square-wave laser seal pattern embodiment shown in FIG. 2, the preset degree of rotation 31 of the shaft holder fixture is set at 20°. However, in other embodiments, the preset degree of rotation 31 of the shaft holder fixture may range from a low of 1° to a high of 180°, depending on the manufacturing preference and/or equipment specification.

Figure 3:
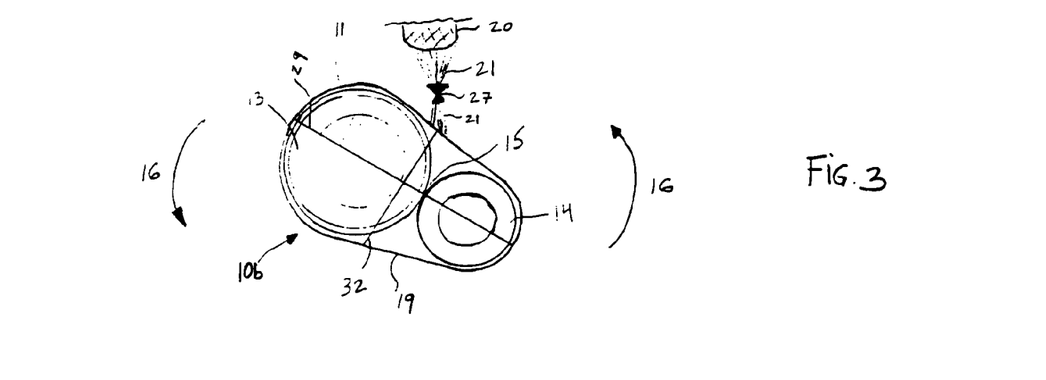
FIG. 3 illustrates the square-wave laser beam used to target and seal a groove between two lumens or shafts of a multiple lumen component.
Figure 4:
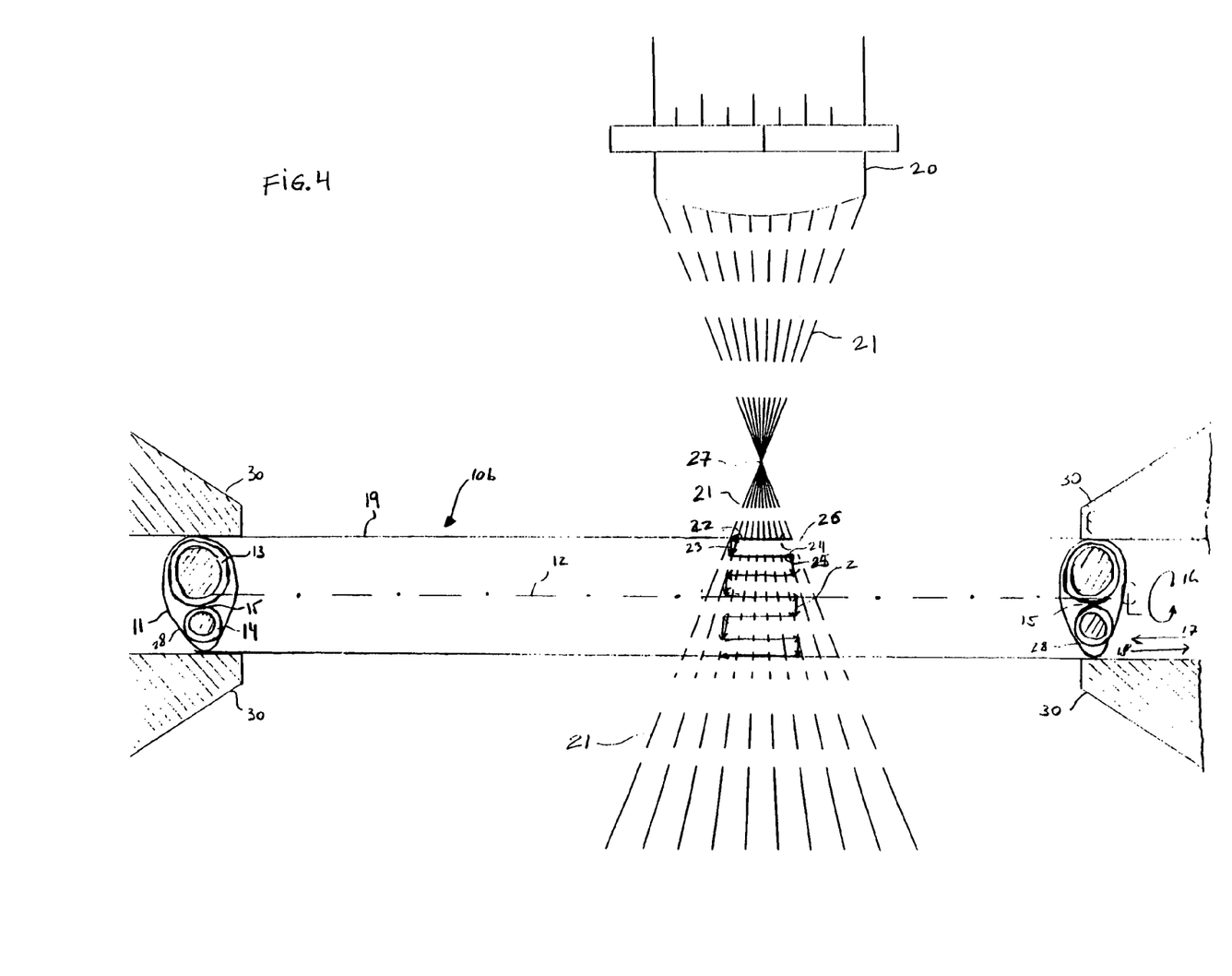
FIG. 4 is a schematic view of the laser device and the holder fixture holding a multi-lumen component while a square-wave laser seal is performed on the multi-lumen component.

With reference to FIGS. 3 and 4, a square-wave seal pattern for bonding two shafts (13, 14) bundled together into an irregular shaped shaft bundle 10b (i.e., non-circular geometry component) is described. The multi-lumen irregular shaped shaft bundle 10b has an outer member 19 enclosing the shafts (13, 14). The shafts (13, 14) have a groove 15 between them. The shape and configuration of groove 15 does not permit shafts (13, 14) to form a fluid tight bond using the conventional helical or rings laser seal pattern 1. By using the square-wave laser seal pattern 2 of the present invention, groove 15 can be targeted with the laser beam 21, thus allowing the shafts (13, 14) to bond well together. Absorption of the laser beam energy by the material of the outer member 19 that is part of the shaft bundle 10b produces the desired melting and sealing of the shaft bundle 10b.

The square-wave laser seal shown in FIGS. 3 and 4 is achieved by using a process similar to the process used to complete the square-wave laser seal of FIG. 2. A laser beam 21 is directed onto the multi-lumen irregular shaped shaft bundle 10b while the shaft bundle 10b is alternately rotated (in a circular direction 16) about its longitudinal axis 12 and horizontally translated (i.e., moved back and forth) along its longitudinal axis 12. Alternating between rotational movement and horizontal movement creates a plurality of vertical laser seal bond segments and horizontal laser seal bond segments. The combination of vertical and horizontal laser seal bond segments creates an uninterrupted fluid tight seal around a circumference 11 of the irregular geometry of the multi-lumen shaft bundle 10b (see FIGS. 3 and 4).

As shown in FIG. 4, to fully achieve the square-wave laser seal pattern 2 of this invention, the multi-lumen shaft bundle 10b is alternately rotated about or horizontally translated (or moved) along the shaft bundle longitudinal axis 12 until the square-wave laser seal pattern 2 fully encircles the entire circumference 11 of the shaft bundle 10b. Similar to the square-wave laser seal of FIG. 2, in the embodiment of the present invention illustrated in FIGS. 3 and 4 the multi-lumen shaft bundle 10b being held by the shaft holder fixture 30 may be rotated in a clockwise or counter-clockwise circular direction 16 along longitudinal axis 12.

As shown in FIG. 4, the seal pattern 2 may either be started by initially creating a first horizontal laser seal bond segment 22 or by initially creating a first vertical laser seal bond segment 23. As with the square-wave laser seal pattern embodiment shown in FIG. 2, at least two horizontal laser seal bond segments (22, 24) and two vertical laser seal bond segments (23, 25) must be completed so that the square-wave laser seal pattern 2 fully encircles the circumference 11 of the multi-lumen irregular shaped shaft bundle 10b.

In the multi-lumen irregular shaped shaft embodiment, the lengths of the horizontal laser seal bond segments (22, 24) define a "width" 26 of the square-wave laser seal pattern shown in FIG. 4. In this embodiment, the lengths of the horizontal laser seal bond segments (22, 24), and thus the square-wave laser seal "width" 26, are approximately 0.25 mm, with an upper range length limit of approximately 1.5 mm. These horizontal laser seal bond segment lengths are applicable to sealing irregular shaped shafts and balloons used in PTCA applications, for example a multi-lumen balloon radiation centering catheter. Larger horizontal laser seal bond segment lengths of between 0.5-5 mm may be used to seal irregular shaped shafts used in applications other than PTCA applications.

For the embodiment shown in FIGS. 3 and 4, the laser device 20 emitting the laser beam 21 is held in a fixed position while the shaft holder fixture 30 holding the multi-lumen irregular shaped shaft bundle 10b is in a movable configuration. Depending on the laser device configuration used and laser seal manufacturing preferences, in other embodiments the laser device 20 may be moved along and/or around the multi-lumen irregular shaped shaft bundle 10b while the shaft bundle 10b is kept either in a fixed or movable position by the shaft holder fixture 30.

The shaft holder fixture 30 with the multi-lumen irregular shaped shaft bundle 10b is generally incrementally rotated along its longitudinal axis 12 based on a preset degree of rotation 31 of the shaft holder fixture 30. For the square-wave laser seal pattern embodiment shown in FIGS. 3 and 4, the preset degree of rotation 31 of the shaft holder fixture is set at 20°. However, in other embodiments, the preset degree of rotation 31 of the shaft holder fixture may range from a low of 1° to a high of 180°, depending on the manufacturing preference and/or equipment specification.

One significant feature differentiating the process used to achieve the square-wave laser seal shown in FIGS. 3 and 4 from the process used to achieve the square-wave laser seal shown in FIG. 2 is the horizontal translation speed rate of the shaft holder fixture 30. Recall that in the seal process used for the seal shown in FIG. 2, the horizontal translation speed rate of the shaft holder fixture 30 is kept at a pre-determined constant value. In contrast, for the seal shown in FIGS. 3 and 4, the horizontal translation speed rate of the shaft holder fixture 30 may be decreased or increased from the pre-determined horizontal translation speed rate value. By decreasing the horizontal translation speed rate, the laser beam energy (i.e., heat) deposited onto a shaft bundle 10b region will increase. Conversely, by increasing the horizontal translation speed rate of the shaft bundle 10b, the heat deposited onto a shaft bundle 10b region by the laser beam 21 will decrease.

Changing the horizontal translation speed rate is dependent on such variables as: (a) how far the multi-lumen shaft bundle 10b is from a focal point 27 of the laser beam 21, (b) whether the laser beam 21 passes any "thin walled" regions 28 within the multi-lumen shaft bundle 10b, and (c) whether the laser beam 21 passes any grooves 15 within the multi-lumen shaft bundle 10b.

Figure 5A:
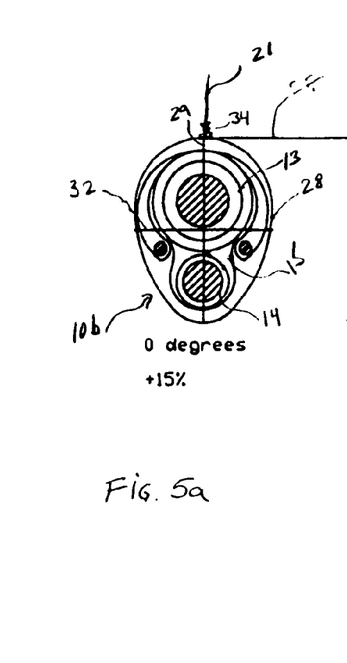
FIGS. 5*a*-5*e* illustrate an example of the variable horizontal translation speed of the holder fixture while performing the square-wave laser seal around a multi-lumen component.

With reference to FIGS. 4 and 5a-5e, in a multi-lumen shaft bundle 10b having an "egg-shaped" cross-sectional profile, the horizontal translation speed rate of the shaft holder fixture 30 (with the multi-lumen shaft bundle 10b) would generally be increased from a pre-determined speed rate value when a shaft bundle major axis 29 is positioned in a parallel direction to the direction of the laser beam 21 (see FIG. 5a). Referring to FIG. 5a again, for example, when the preset degree of rotation 31 of the shaft holder fixture is generally set at 0° relative to the shaft bundle major axis 29, the horizontal translation speed rate for the shaft holder fixture 30 would be increased by 15% from the pre-determined horizontal translation speed rate. It should be noted that the percent increase may vary depending upon the particular configuration being sealed. The increase in the horizontal translation speed rate for the shaft holder fixture 30 allows the seal area 34 to receive the desired amount of heat from the laser beam 21, thus eliminating the possibility of "heat thinning" shaft bundle material 19 thus creating a tight seal segment around circumference 11 of the shaft bundle 10b.

Figure 5B:
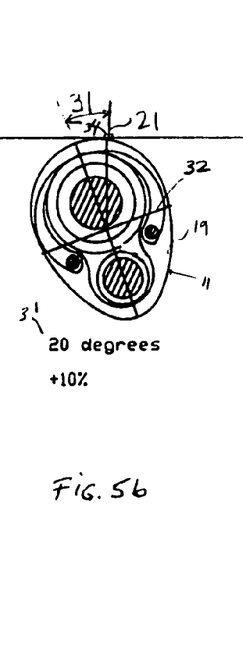
Figure 5C:
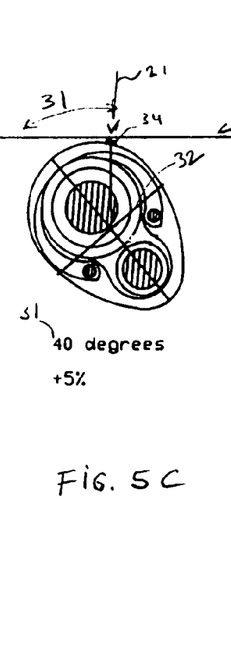
Figure 5D:
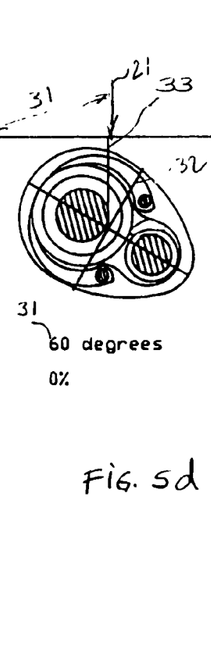

With reference to FIGS. 5b-5d, as the multi-lumen shaft bundle 10b is rotated in a circular direction 16 along its longitudinal axis 12 according to the preset degree of rotation 31, the direction of the major axis 29 may no longer be parallel to the direction of the laser beam 21. As the distance 33 from the laser beam focus 27 to the surface of the multi-lumen shaft bundle 10b increases, the amount of heat required to properly achieve a tight seal segment increases. Therefore, the horizontal translation speed rate of the shaft holder fixture 30 (with the multi-lumen shaft bundle 10b) would generally be decreased. For example, the horizontal translation speed rate may be decreased until it reaches the pre-determined speed rate.

Figure 5E:
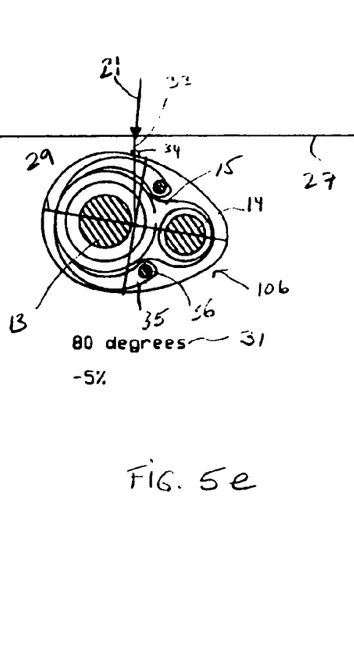

Referring to FIG. 5e, as the multi-lumen shaft bundle 10b is further rotated in a circular direction 16 along its longitudinal axis 12 according to the preset degree of rotation 31, the direction of the major axis 29 is close to a perpendicular direction relative to direction of the laser beam 21. In this configuration, the minor axis 32 is positioned in a parallel direction to the direction of the laser beam 21. Since the distance 33 from the laser beam focus 27 to the surface of the multi-lumen shaft bundle 10b has increased, the amount of heat required to properly achieve a tight seal segment has increased even further. Therefore, the horizontal translation speed rate of the shaft holder fixture 30 (with the multi-lumen shaft bundle 10b) would generally be decreased even further. For example, the horizontal translation speed rate may be decreased to a value lower than the pre-determined speed rate.

Referring to FIG. 5e, for example, when the preset degree of rotation 31 of the shaft holder fixture is generally set at 80° relative to the shaft bundle major axis 29, the horizontal translation speed rate for the shaft holder fixture 30 would be decreased by 5% from the pre-determined translation speed rate. The decrease in the horizontal translation speed rate for the shaft holder fixture 30 allows the seal area 34 to receive the desired amount of heat from the laser beam 21, thus creating a tight seal segment.

Using an approach similar to the seal approach shown in FIG. 5e, to properly seal the groove 15 between two lumens of a dual lumen shaft 10b, the quantity of heat from laser beam may be increased by reducing the horizontal translation speed rate for the shaft holder fixture 30. Furthermore, in shaft bundle regions 28 where heat thinning may occur, for example, heating a thin walled material 35 around a mandrel 36, the horizontal translation speed rate for the shaft holder fixture 30 would be increased from a pre-determined horizontal translation speed rate so as to reduce the amount of heating in the region around the mandrel.

Figure 6:
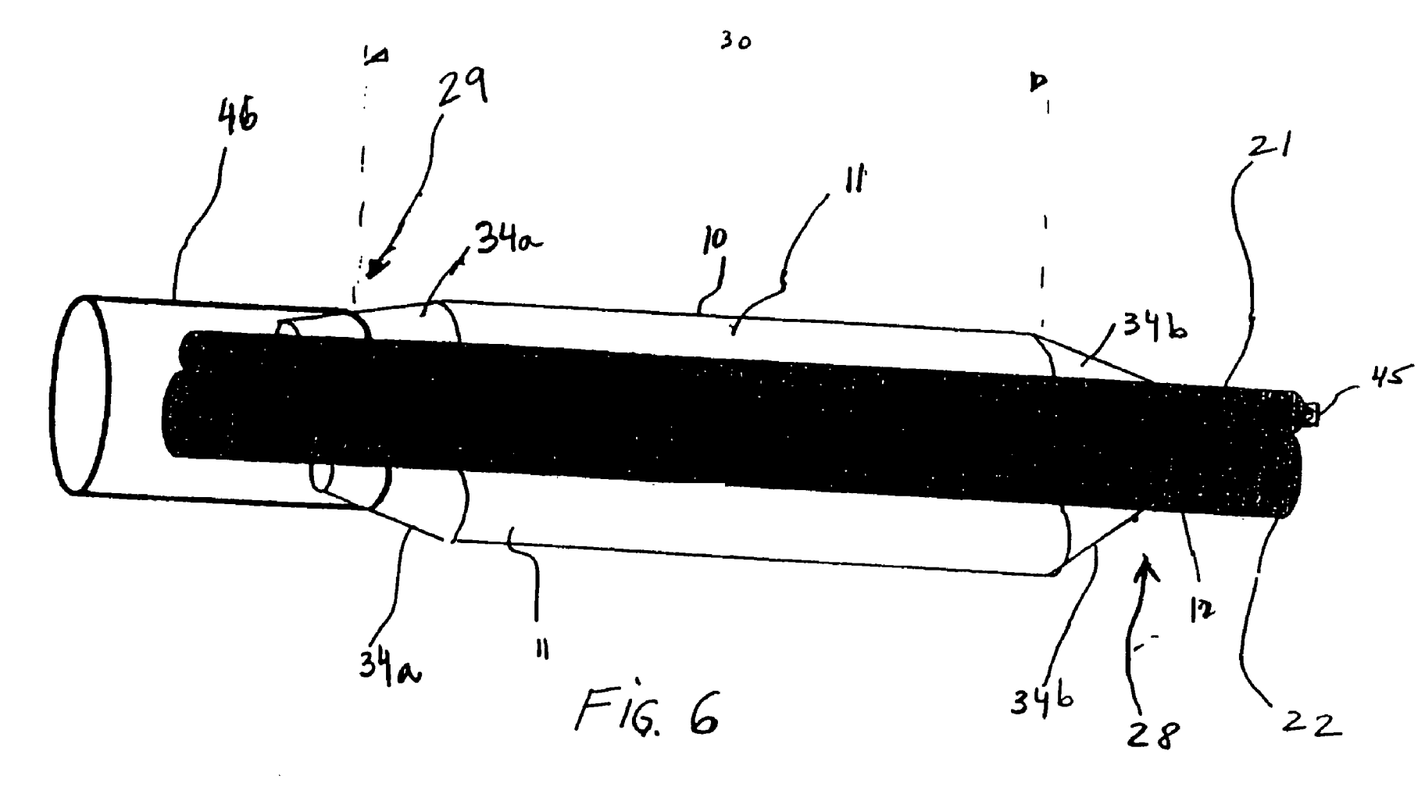
FIG. 6 illustrates an example of an inflated multi-lumen balloon having fluid tight seals formed using the square-wave laser seal pattern of the present invention.

Referring to FIG. 6, an example of an inflated multi-lumen balloon having fluid tight seals formed using the square-wave laser seal pattern of the present invention is shown. The multi-lumen balloon 10 has a guidewire lumen 21 extending through one of the balloon outer lumens 11 is shown. Note that one of the outer lumens is hidden from view. A radiation source lumen 22 (capable of holding a radiation source) extends lengthwise through the balloon central lumen 12. The outer lumen 11 with the guidewire lumen 21 extending through it is also inflated as part of the function of the centering balloon catheter. Continuing with reference to FIG. 17, the multi-lumen balloon 10 has a distal seal 28 and a proximal seal 29. Distal seal 28 seals the plurality of distal ends 34b of the balloon outer lumens 11 to a catheter shaft (formed by the radiation source lumen 22 and guidewire lumen 21) while the proximal seal 29 seals the plurality of proximal ends 34a of the balloon outer lumens 11 to the catheter shaft. When balloon outer lumens' distal and proximal ends (34b, 34a) are sealed together into the distal seal and proximal seal respectively (28, 29), each of the outer lumens 11 takes the form of a "flute" (i.e., an elongated cylinder having tapered ends) when inflated by an inflation medium.

A square-wave laser seal pattern and seal around the circumference of a shaft to bond materials and method for providing the same has been described. Although specific embodiments, including specific parameters, methods, and materials have been described, various modifications to the disclosed embodiments will be apparent to one of ordinary skill in the art upon reading this disclosure. Therefore, it is to be understood that such embodiments are merely illustrative of and not restrictive on the broad invention and that this invention is not limited to the specific embodiments shown and described.

We claim:

1. A method to seal a catheter shaft bundle, the method comprising:
    directing a laser beam onto the catheter shaft bundle having at least two catheter shafts while the catheter shaft bundle is moving in a horizontal direction at a variable speed relative to a laser device so as to create a horizontal laser seal bond segment; and
    directing the laser beam onto the catheter shaft bundle while rotating the catheter shaft bundle about a shaft longitudinal axis so as to create a vertical laser seal bond segment, wherein the catheter shaft bundle is alternately rotated between moving in the horizontal direction and the longitudinal axis, the vertical laser seal bond segment coupled with the horizontal laser seal bond segment so as to form a square-wave laser seal around a complete circumference of the catheter shaft bundle that seals an inner surface of an outer member to an outer perimeter surface of at least one catheter shaft.

2. The square-wave laser seal pattern of claim 1, wherein at least two square-wave laser seal pattern sections are formed, and wherein the square-wave laser seal fully encircles the complete circumference of the catheter shaft bundle and seals the entire inner surface of the outer member to at least two outer surface portions of at least two catheter shafts.

3. The square-wave laser seal pattern of claim 1, wherein the horizontal laser seal bond segment is between 0.25-1.5 mm.

4. The square-wave laser seal pattern of claim 2, wherein the at least two square-wave laser seal pattern sections formed are coupled together around the circumference of the shaft bundle.

5. The square-wave laser seal pattern of claim 1, wherein the shaft bundle is rotating about the shaft bundle longitudinal axis at a preset degree of rotation of between 1-180° relative to the laser beam.

6. The square-wave laser seal pattern of claim 1, wherein the shaft bundle is rotating about the shaft bundle longitudinal axis at a preset degree of rotation of approximately 20° relative to the laser beam.

7. A method to seal a catheter shaft bundle, the method comprising:
    directing a laser beam onto the catheter shaft bundle having at least two catheter shafts while rotating the catheter shaft bundle about a shaft bundle longitudinal axis so as to create a vertical laser seal bond segment; and
    directing the laser beam onto the catheter shaft bundle while the catheter shaft bundle is moving in a horizontal direction at a variable speed relative to a laser device so as to create a horizontal laser seal bond segment, wherein the catheter shaft bundle is alternately rotated between moving about the longitudinal axis and the horizontal direction, the horizontal laser seal bond segment coupled with the vertical laser seal bond segment so as to form a square-wave laser seal around a complete circumference of the catheter shaft bundle that seals an inner surface of an outer member to an outer perimeter surface of at least one catheter shaft.

8. The square-wave laser seal pattern of claim 7, wherein at least two square-wave laser seal pattern sections are formed, and wherein the square-wave laser seal fully encircles the complete circumference of the catheter shaft bundle and seals the entire inner surface of the outer member to at least two outer surface portions of at least two catheter shafts.

9. The square-wave laser seal pattern of claim 7, wherein the horizontal laser seal bond segment is between 0.25-1.5 mm.

10. The square-wave laser seal pattern of claim 8, wherein the at least two square-wave laser seal pattern sections formed are coupled together around the circumference of the shaft bundle.

11. The square-wave laser seal pattern of claim 7, wherein the shaft bundle is rotating about the shaft bundle longitudinal axis at a preset degree of rotation of between 1-180° relative to the laser beam.

12. The square-wave laser seal pattern of claim 7, wherein the shaft bundle is rotating about the shaft bundle longitudinal axis at a preset degree of rotation of approximately 20° relative to the laser beam.

13. A method to seal a catheter shaft bundle, the method comprising:
directing a laser beam into the catheter shaft bundle having at least two catheter shafts while the catheter shaft bundle is moving in a horizontal direction along a shaft bundle longitudinal axis at a variable speed relative to a laser device so as to create a horizontal laser seal bond segment;
directing the laser beam into the catheter shaft bundle while the shaft bundle is moving in a rotational direction about the shaft bundle longitudinal axis at a variable speed relative to the laser device so as to create a vertical laser seal bond segment; and
alternating between directing the laser beam into the catheter shaft bundle while the catheter is moving in the horizontal direction, and directing the laser beam into the catheter shaft bundle while the shaft bundle is moving in the rotational direction, wherein the vertical laser seal bond segment is coupled to the horizontal laser seal bond segment so as to form a square-wave laser seal around a complete circumference vertically around a shaft bundle vertical perimeter of the catheter shaft bundle that seals an inner surface of an outer member to an outer perimeter surface of at least one catheter shaft.

14. The method of claim 13, wherein the variable speed alternates between a constant speed and stopped to form the square-wave laser seal pattern section.

15. The method of claim 1 wherein the square-wave laser seal pattern is a square-wave weld along a non-circular, irregular shaped circumference of the shaft bundle.

16. The method of claim 7 wherein the square-wave laser seal pattern is a square-wave weld along a non-circular, irregular shaped circumference of the shaft bundle.

17. The method of claim 13 wherein the square-wave laser seal pattern is a square-wave weld along a non-circular, irregular shaped circumference of the shaft bundle.

18. A method to seal a catheter shaft bundle, the method comprising:
directing a laser beam into the catheter shaft bundle while the catheter shaft bundle is moving in a horizontal direction along a shaft bundle longitudinal axis at a variable speed relative to a laser device so as to create a horizontal laser seal bond segment;
directing the laser beam into the catheter shaft bundle while the shaft bundle is moving in a rotational direction about the shaft bundle longitudinal axis at a variable speed relative to the laser device so as to create a vertical laser seal bond segment; and
alternating between directing the laser beam into the catheter shaft bundle while the catheter is moving in the horizontal direction, and directing the laser beam into the catheter shaft bundle while the shaft bundle is moving in the rotational direction, wherein the vertical laser seal bond segment is coupled to the horizontal laser seal bond segment so as to form a square-wave laser seal around a complete circumference vertically around a shaft bundle vertical perimeter of the catheter shaft bundle that seals an inner surface of a balloon to an outer perimeter surface of a balloon catheter.

19. The method of claim 1, wherein the catheter shaft bundle, the outer member, and the at least one catheter shaft made of biocompatible material for insertion into vessels of the cardiovascular system.

20. The method of claim 18, wherein the catheter shaft bundle, the balloon, and the balloon catheter are made of biocompatible material for insertion into vessels of the cardiovascular system.

21. The method of claim 1, wherein the square wave laser seal around the complete circumference provides shear strength and support in a direction parallel to and in a direction tangential to the complete circumference of the catheter shaft bundle.

22. The method of claim 18, wherein the square wave laser seal around the complete circumference provides shear strength and support in a direction parallel to and in a direction tangential to the complete circumference of the catheter shaft bundle.

* * * * *